(12) United States Patent
Kim et al.

(10) Patent No.: US 11,045,572 B1
(45) Date of Patent: Jun. 29, 2021

(54) BOOSTER DEVICE FOR AROMA DISPLAY

(71) Applicant: AROMAJOIN CORPORATION, Kyoto (JP)

(72) Inventors: Dong Wook Kim, Kyoto (JP); Kazuhiro Nakano, Kyoto (JP)

(73) Assignee: AROMAJOIN CORPORATION, Kyoto (JP)

( * ) Notice: Subject to any disclaimer, the term of this patent is extended or adjusted under 35 U.S.C. 154(b) by 0 days.

(21) Appl. No.: 17/258,177

(22) PCT Filed: Oct. 23, 2019

(86) PCT No.: PCT/JP2019/041464
§ 371 (c)(1),
(2) Date: Jan. 6, 2021

(87) PCT Pub. No.: WO2020/194818
PCT Pub. Date: Oct. 1, 2020

(30) Foreign Application Priority Data

Mar. 28, 2019 (JP) .............................. JP2019-063583

(51) Int. Cl.
*B01F 3/04* (2006.01)
*A61L 9/14* (2006.01)
(Continued)

(52) U.S. Cl.
CPC .............. *A61L 9/122* (2013.01); *A61L 9/032* (2013.01); *A61L 9/125* (2013.01); *B01F 3/04* (2013.01);
(Continued)

(58) Field of Classification Search
CPC ........ B01F 3/04; B01F 3/04085; A61L 9/122; A61L 9/14; A61L 9/032; A61L 9/125
See application file for complete search history.

(56) References Cited

U.S. PATENT DOCUMENTS 10,596,293 B2 * 3/2020 Hsiao ..................... B01D 35/30
2011/0061400 A1   3/2011 Park et al.
(Continued)

FOREIGN PATENT DOCUMENTS

CN       102019866 A    4/2011
CN       207262628 U    4/2018
(Continued)

OTHER PUBLICATIONS

Official Communication issued in International Patent Application No. PCT/JP2019/041464, dated Dec. 10, 2019.
(Continued)

*Primary Examiner* — Robert A Hopkins
(74) *Attorney, Agent, or Firm* — Keating and Bennett, LLP

(57) ABSTRACT

A booster device for an aroma display is able to increase or decrease air flow to carry a scent emitted from an aroma cartridge. The aroma display includes a columnar shape with first and second surfaces and a side surface, an emitting opening to emit a scent is provided on the first surface, and a wind source to emit the scent to an exterior of aroma display is provided in the aroma display. The booster device includes a housing including the aroma display therein, and a fan provided in the housing on the side of the second surface of aroma display. The housing includes a cylindrical outer housing and a holder to hold the aroma display in the housing. The holder holds the aroma display to define an air passage for the wind from the fan between the outer housing and the aroma display.

13 Claims, 13 Drawing Sheets

(51) Int. Cl.
  *A61L 9/12*   (2006.01)
  *A61L 9/03*   (2006.01)
(52) U.S. Cl.
  CPC ...... *A61L 2209/11* (2013.01); *A61L 2209/132* (2013.01); *A61L 2209/133* (2013.01)

(56)  References Cited

U.S. PATENT DOCUMENTS

2015/0283282 A1   10/2015   Kim et al.
  2016/0021325 A1    1/2016   Porcar

FOREIGN PATENT DOCUMENTS

CN    109224110 A    1/2019
  JP     50-124193 U   10/1975
  JP     55-008734 A    1/1980
  JP    2014-092673 A   5/2014
  JP    2014-092674 A   5/2014
  WO      97/39779 A1  10/1997

OTHER PUBLICATIONS

Official Communication issued in Japanese Patent Application No. 2019-063583, dated Jul. 2, 2019.

\* cited by examiner

BOOSTER DEVICE FOR AROMA DISPLAY

BACKGROUND OF THE INVENTION

1. Field of the Invention

The present invention relates to an aroma display and, more specifically, to an improvement of an aroma display that is able to emit different scents by holding a plurality of aroma cartridges.

2. Description of the Related Art

Human communication is performed in various modes based on human senses. Most frequently used are visual and auditory communications. By contrast, olfaction or sense of smell, on which humans rely considerably, is hardly used in communication. However, if the sense of smell can be utilized in addition to visual and auditory senses, communication would be more effective and various people would be able to share their experiences more profoundly.

Focusing on this point, recently, devices have been proposed which are used with audio-visual reproducing devices, for example, television receivers, personal computers and game machines to generate scents fitting for the time and place. In the present specification, a device that generates scents fitting for scenes will be referred to as an "aroma display".

Emission of a certain scent supposed to be fit for a certain scene would not be very effective if there is any lingering scent produced immediately before. Therefore, a desirable aroma display is one that is able to diffuse a desired scent in a certain limited scope at one time point and is able to blow out that scent and switch to another scent at another time point.

Without the ability to freely switch from one scent to another, an aroma display cannot make full use of scents. For this purpose, one possible approach is to prepare a plurality of cartridges (referred to as aroma cartridges), each containing a pre-selected scent emission source (referred to as a scent source), to load an aroma display with them, and emit the desired scent via the relevant cartridge.

A scent channel for carrying the scent from the scent source in the cartridge is formed in the cartridge, and a mechanism for feeding air into the cartridge at desired times is provided by the aroma display, so that the scent is emitted through the channel to the aroma display's exterior. Aside from the mechanism that emits scents from the cartridges, the aroma display also provides a mechanism for emitting air free of any scent component, having an air emission opening near the scent channels. To switch scents after one scent is emitted, the air-emitting mechanism emits a blast of air to blow out the scented air, and then another scent is emitted. Thus, scents can be switched at any timing, avoiding improper blending of scents.

Such a technique is disclosed in JP2014-092673A. The technique disclosed in JP2014-092673A is as described above. An opening is formed in the housing of an aroma display for emitting the scent to the outside. The scent channels, from their respective aroma cartridges and air emission openings, are all connected to this opening. Each aroma cartridge is releasably held in the housing of the aroma display. An opening for introducing air into the aroma cartridge is formed at a prescribed portion of each aroma cartridge. At the portion of the aroma display which corresponds to this opening when an aroma cartridge is held by the aroma display, a wind source containing a diaphragm with a piezoelectric element attached is mounted corresponding to each aroma cartridge. By applying an AC voltage to the piezoelectric element, the diaphragm vibrates and introduces air into the aroma cartridge through a nozzle provided on the wind source and through the opening of the aroma cartridge. From the aroma cartridge that received the introduced air, scented air corresponding to the scent source therein is emitted to the outside through the scent channel.

Further, at the portion corresponding to the root of air emission opening of the aroma display, a wind source is provided as an air-emitting mechanism, which, having a structure similar to that of the wind sources attached to the aroma cartridges, can feed a larger amount of air, free of any scent, with stronger force, to the air emission opening.

The aroma display having the above-described structure is able to freely switch scents by selecting the wind source or sources to be operated. Further, by simultaneously operating the air-emitting mechanism for emitting scent-free air, it is possible to prevent the undesired blending of scents. The wind source to be operated and its timing may be controlled by sending an external command to the aroma display. Therefore, the aroma display can achieve magnificent effects of emitting desired scents appropriately by causing the desired wind sources to operate, for example, at desired timings in movies or animated films.

Because the conventional aroma display uses piezoelectric elements as wind sources in the mechanisms for emitting air and scent, it has the following drawbacks. While a wind source using a piezoelectric element can suppress the noise level, it can feed only a small amount of air. It poses no problem when the distance between the aroma display and a user is short, as in the case where the aroma display is used as an accessory of a PC. However, when it is used in a wider space, for example, when multiple people watch a TV, it is difficult to spread a scent far and wide or to dissipate the emitted scent immediately.

In order to solve such problems, it is possible to provide the wind source of the air emission mechanism with a stronger fan. In that case, however, the fan noise would be problematic, and the aroma display would be larger. Further, a larger fan leads to a problem in which it becomes difficult to maintain the emission of scent to a limited small area near the aroma display. A desirable aroma display is one that can emit a large volume of air to spread a scent far and wide, can dissipate the emitted scent, and can also emit a scent in a controlled manner within a limited space.

SUMMARY OF THE INVENTION

Preferred embodiments of the present invention provide booster devices that are each able to increase and decrease a volume of air flow that carries scents emitted from aroma cartridges.

According to a first preferred embodiment of the present invention, a booster device of an aroma display is able to significantly improve the scent-emitting ability of the aroma display. The aroma display has a columnar shape including first and second surfaces and a side surface. The first surface includes an emitting opening to emit a scent. A wind source to emit the scent to an exterior of the aroma display is provided in the aroma display. The booster device includes a housing including the aroma display, and a fan provided in the housing. The housing includes a cylindrical outer housing including an air inlet to take in air and a holder holding the aroma display in the housing. The holder holds the aroma display to define an air passage, through which air from the fan passes, between the outer housing and the aroma display.

Preferably, for example, both the aroma display and the outer housing have a central axis, and the holder holds the aroma display with central axes of the aroma display and the outer housing are parallel or substantially parallel to each other.

More preferably, for example, the holder holds the aroma display to align the central axis of the aroma display with the central axis of the outer housing.

More preferably, for example, the booster device for an aroma display further includes a conical or substantially conical structure that narrows the air flow generated by the fan, provided at an end portion of the outer housing on the side of the first surface of the aroma display.

Preferably, for example, the booster device for an aroma display further includes a heater provided in the air passage to heat air passing through the air passage.

More preferably, for example, the booster device for an aroma display further includes a heat exchanger provided in the outer housing to conduct heat exchange between the air passing through the air passage and air outside the outer housing.

More preferably, for example, the heat exchanger is provided to discharge heat of the air passing through the air passage to an exterior of the outer housing and to cool the air passing through the air passage.

Preferably, for example, the heat exchanger is provided to introduce heat of the air outside the outer housing into the outer housing to heat the air passing through the air passage.

More preferably, for example, an opening is provided on a side surface of the outer housing, the heat exchanger includes a Peltier module including first and second surfaces to contact respective objects of heat exchange, and the Peltier module is attached to the opening with the first surface facing the air passage and the second surface facing outside of the outer housing.

More preferably, for example, the booster device for an aroma display further includes a heat sink provided on the second surface of the Peltier module, the Peltier module includes an upper edge with a same or substantially same length as an edge at the upper end of the opening, and the upper edge is in contact with the edge at the upper end of the opening, and a lower end side of the Peltier module is located at a position to split air flow generated by the fan to the air passage side and to the heat sink side by the Peltier module.

More preferably, for example, the booster device for an aroma display further includes a heat insulator located between the air passage and the aroma display.

More preferably, for example, the heat insulator is provided between the air passage and at least a portion of the aroma display which holds a scent component.

A booster device of an aroma display may include a plurality of fans, and the plurality of fans may be located at equal or substantially equal intervals around the aroma display in the housing.

The fan may be provided in the housing between the second surface and the bottom surface of the housing.

The above and other elements, features, steps, characteristics, and advantages of the present invention will become more apparent from the following detailed description of the preferred embodiments with reference to the attached drawings.

DETAILED DESCRIPTION OF THE PREFERRED EMBODIMENTS

Figure 1:
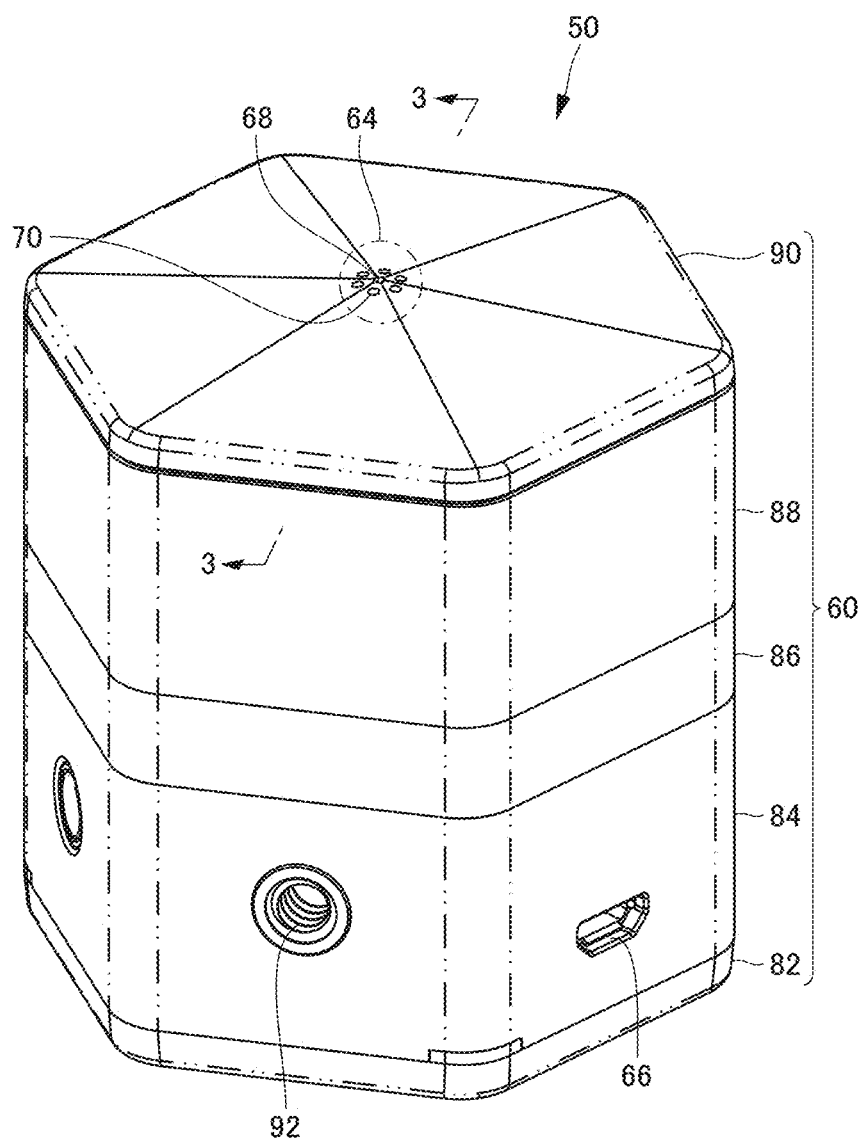
FIG. 1 is an oblique downwards perspective view of an aroma display according to a preferred embodiment of the present invention.

In the following description and in the drawings, the same components are denoted by the same reference characters. Therefore, detailed description thereof will not be repeated. It is to be understood that not every component of the preferred embodiments described below is indispensable for the present invention. Some of the components may be omitted or replaced by other features or structures of any of the various preferred embodiments of the present invention.

Figure 2:
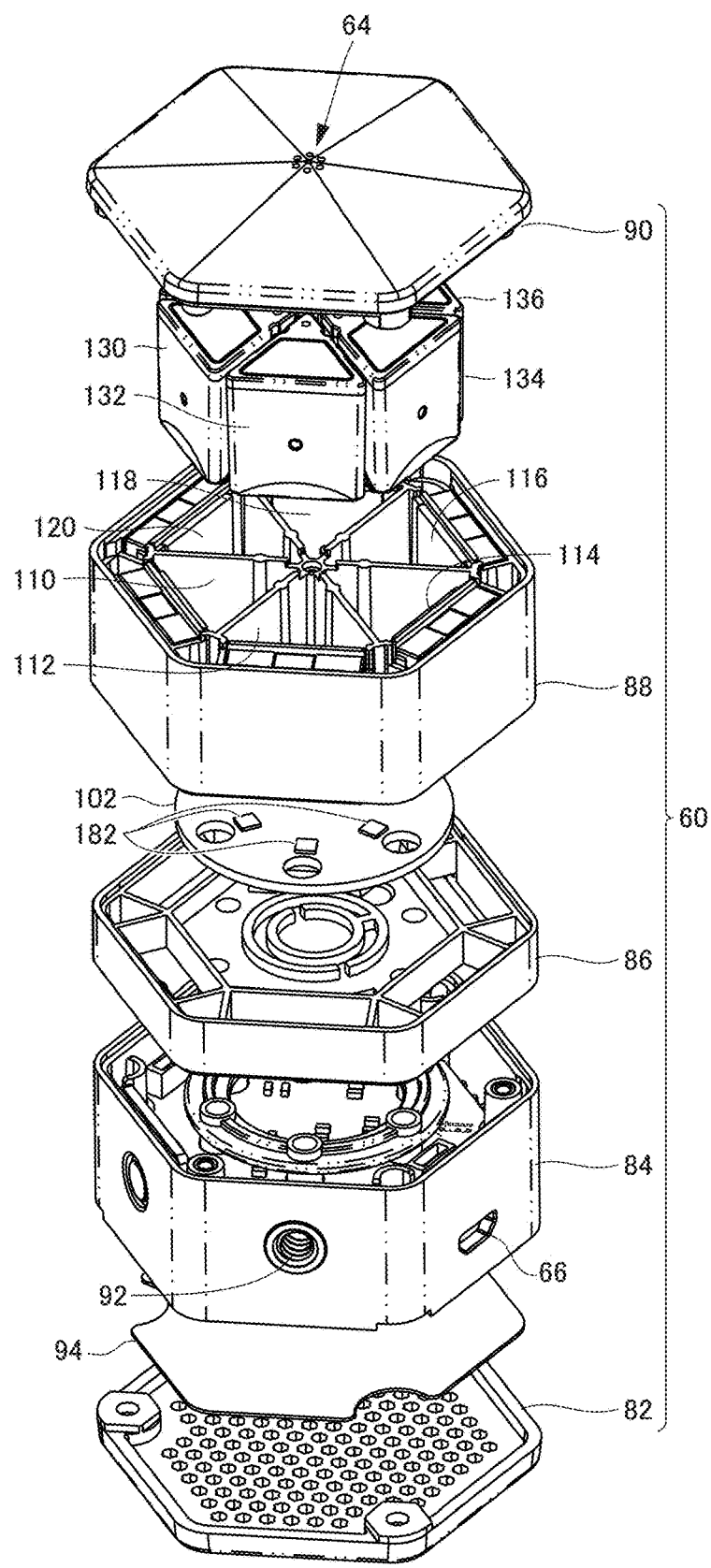
FIG. 2 is an exploded, oblique downwards perspective view of the aroma display shown in FIG. 1.

FIG. 1 shows an appearance of an aroma display 50 that is secured in a booster device of an aroma display in accordance with a first preferred embodiment of the present invention. As shown in FIG. 1, an aroma display 50 includes a housing 60 that is a hexagonal or substantially hexagonal column with a central axis. FIG. 2 is an exploded perspective view of the aroma display 50, and FIG. 3 is a cross-sectional view taken along the line 3-3 in FIG. 1 of the aroma display 50.

Figure 3:
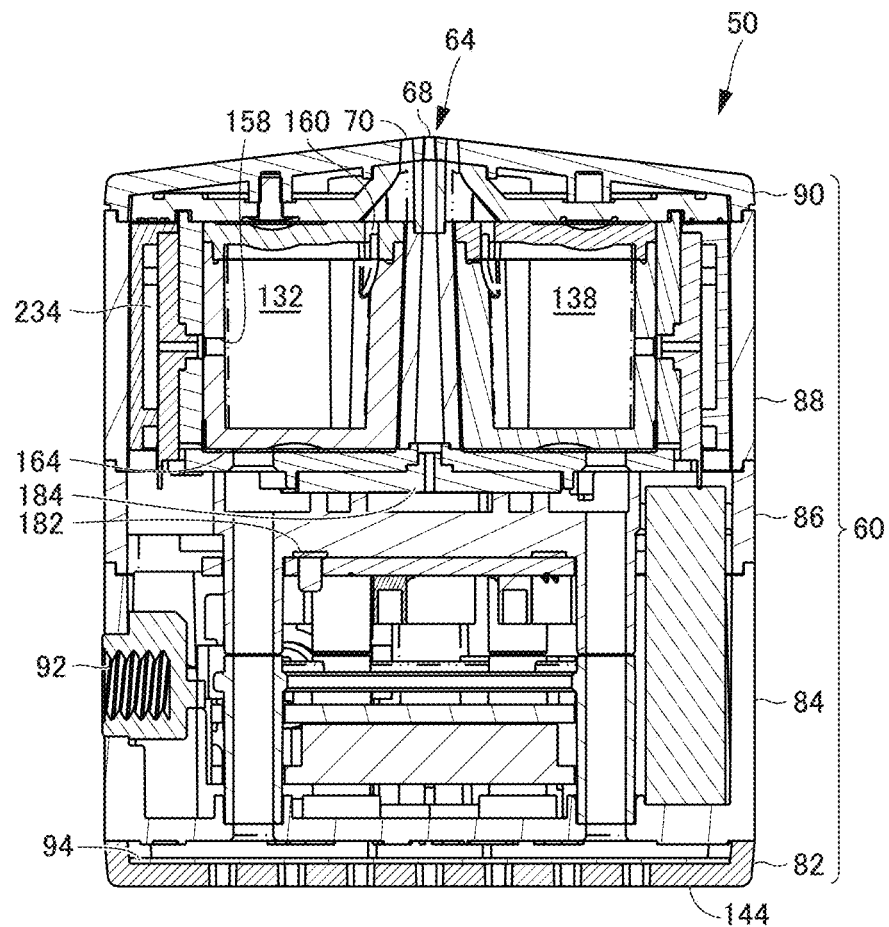
FIG. 3 is a cross-sectional view take along the line 3-3 of the aroma display shown in FIG. 1.

Referring to FIGS. 1 to 3, the housing 60 includes a base panel 82, a base body 84 located above the base panel 82 and attached to the base panel 82 by screws, for example, a middle body 86 fitted to the base body 84 from above base body 84, an upper body 88 fitted to the top of the middle body 86, the upper body 88 including a cartridge loading section opening upward, which may be loaded with six aroma cartridges, and an upper panel 90 fitted to the upper body 88 to close the upper opening of the upper body 88. By removing the upper panel 90, the opening of the upper body 88 is exposed, and a user is able to access the aroma cartridge loading section to load or unload the loading section with aroma cartridges.

In the present preferred embodiment, the upper body 88 includes a slightly rounded hexagonal cross-section, and the cartridge loading sections 110, 112, 114, 116, 118, and 120, which may be loaded with, for example, six aroma cartridges 130, 132, 134, 136, and 138, (aroma cartridge 138 is shown in FIG. 3) are provided inside the upper body 88. Accordingly, as shown in FIG. 2, the aroma cartridges 130, . . . are included in the upper body 88. As an example, on a bottom surface of the aroma cartridge 132, an NFC tag 164 (see FIG. 3) is attached, and at a nearby portion of the upper body 88, six NFC chips, for example, NFC chip 182 that is able to wirelessly communicate with the NFC tag 164, are provided. The aroma display 50 has a hexagonal or substantially hexagonal column shape including an upper surface, a bottom surface and a side surface, with a central axis.

On a side surface of the base body 84, a screw hole 92 is provided as shown in FIGS. 1 to 3, to which a tripod may be screwed in. The screw hole 92 may meet a specific standard to fit a tripod for a camera or the like.

Referring to FIG. 2, the base body 84 includes a control board including a communication device mounted thereon to wirelessly communicate to/from an exterior of the aroma display 50, and control circuitry to drive micro blowers, which will be described later, and a battery as the power source thereof. Between the middle body 86 and the upper body 88, an NFC chip stage 102 is provided, on which NFC chips 182 and the like communicating with NFC tags 164 provided at the bottoms of aroma cartridges 130 are mounted. Further, on the base panel 82, a plurality of small holes are provided to take in air to generate power to blow out scented air from the aroma cartridges 130. A filter 94 is provided between the base panel 82 and the base body 84 to filter out dust from the introduced air.

NFC tags 164 of the aroma cartridges 130, store ID codes of the scents included in respective aroma cartridges 130. When the aroma display 50 is loaded with the aroma cartridges 130, NFC tags 164 communicate with corresponding NFC chips 182 and transmit ID codes of the scents included in the aroma cartridges 130 to NFC chips 182. NFC chips 182 transmit these ID codes to an external PC or the like through wireless communication. Accordingly, the external PC or the like recognizes the ID codes of respective scents of the aroma cartridges 130 included in the aroma display 50, and the external PC or the like is able to the control aroma display 50 to emit scents in accordance with a program.

Referring to FIGS. 1 to 3, at a central portion of an upper panel 90 of the housing 60, an opening section 64 is provided. Particularly with reference to FIGS. 1 and 3, at the center of the opening section 64, an opening 68 is provided, from which scent-free air from an air emission mechanism included in the housing 60 is emitted, and around this opening, six openings 70, are provided, from which scents are emitted from six aroma cartridges 130, included in the housing 60.

As described above, the aroma display 50 can be mounted on a tripod for a camera. By mounting the aroma display 50 on a small tripod that can be placed on one's desk, the aroma display 50 is able to be placed by the side of a PC, for example, with the opening section 64 of the aroma display 50 positioned very close to and directed to the user's face. Accordingly, predetermined scents are able to be easily transmitted to the user.

A micro USB connector 66 is provided on a side surface of the housing 60. In this preferred embodiment, a connector 66 feeds power to the aroma display 50 through a USB cable and charges a built-in battery of the aroma display 50. The USB cable does not provide external communication for the circuitries in the aroma display 50. The circuitry inside the aroma display 50 exchanges data with an external device or the like via wireless communication. Accordingly, the inner circuitry of the aroma display 50 may perform data communication via wired communication by the USB cable.

Particularly referring to FIG. 3, at a portion of the lower surface of upper body 88 which is above the NFC chip stage 102, a micro blower 184 defining a mechanism to emit scent-free air is fixed. Mechanisms including a micro blower 184 to feed air to an interior of the aroma cartridges 130 will be described later.

Referring to FIG. 2, the upper body 88 has a substantially hexagonal cross-section as described above. The inner space of the upper body 88 is divided into, for example, six aroma cartridge loading sections 110, 112, 114, 116, 118 and 120, each of which is a space including a regular triangle or substantially regular triangle cross-section. The aroma cartridges 130 are respectively inserted into the cartridge loading sections 110.

Referring to FIG. 3, as an example, the aroma cartridge 132 includes a triangular or substantially triangular prism housing of which a horizontal cross-section is a regular triangle or substantially a regular triangle. At a portion of the upper surface of the housing which faces the opening section 64 when the cartridge loading section is loaded with the aroma cartridge, an opening 160 is provided, which is connected to a hollow space inside the housing of aroma cartridge 132 to emit scented air from the scent source sealed in the housing. At the portion of a side surface which is in contact with an inner surface of the upper body 88, an air feeding opening 158 is provided to feed air from an exterior micro blower 234 to the interior of cartridge 132. On the lower surface of the aroma cartridge 132, an NFC tag 164 is attached, for example, by a sticker, for near-field communication with an NFC chip 182.

At a portion of the inner side surface of the upper body 88 at which the air feeding opening 158 for feeding air into the aroma cartridge is positioned when respective cartridges 130 are included in the cartridge loading sections 110, the micro blower 234 for feeding air into air feeding opening 158 is provided. By driving the micro blower 234, air is fed to the interior of the aroma cartridge 132 and from the opening 160 for emitting scent of the aroma cartridge 132 positioned near the center, scented air is emitted to an exterior of the aroma display 50.

Figure 4:
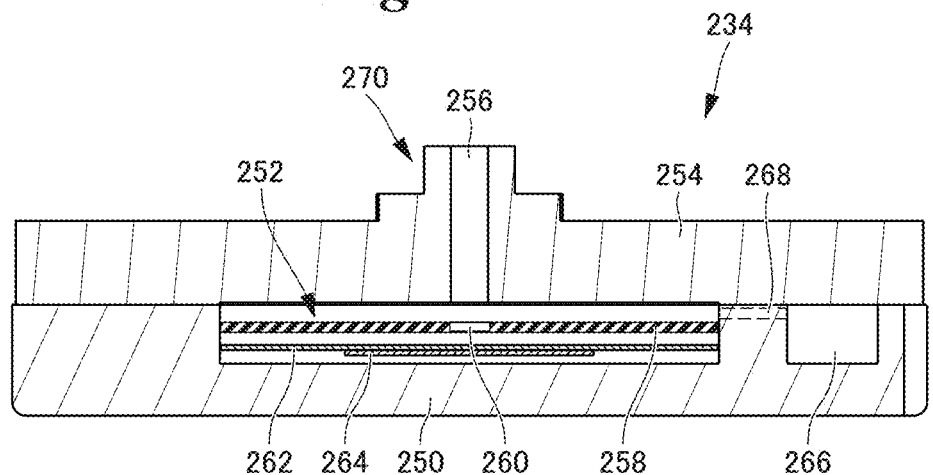
FIG. 4 is an enlarged cross-sectional view of a micro blower.

The micro blower 234 has the same or similar structure as micro blowers disclosed in JP2014-092673A. Referring to FIG. 4, specifically, the micro blower 234 has a case 250 with a blower chamber 252 as an inner space, and a cover 254 with a nozzle 270 provided on its top surface, attached to the case 250 so that it covers the top surface of the case 250 to close the blower chamber 252. An air channel 256 is provided in the nozzle 270, and the air channel 256 opens into the upper portion of the blower chamber 252.

The blower chamber 252 is divided into a upper portion and a lower portion by a partition plate 258. At a position immediately below the air channel 256 of the partition plate 258, an opening 260 is provided and aligned with the air channel 256.

In the lower portion of the blower chamber 252 divided by the partition plate 258, a diaphragm 262 including a thin metal plate with spring resiliency and a piezoelectric element 264 bonded to the lower surface of diaphragm 262 are provided. By applying AC voltage to the piezoelectric element 264, the diaphragm 262 vibrates up and down and emits air through the opening 260 to the blower chamber 252 and further through the air channel 256 to an exterior of the micro blower 234. By positioning the micro blower 234 inside the upper body 88 with the nozzle 270 positioned at the opening on the back side of the aroma cartridge, air is able to be introduced into the aroma cartridge 132 at a predetermined timing for a predetermined time period, and thus, scented air can be emitted from the aroma cartridge 132 and the like. An air intake opening 266 is provided in a case 250, and the air from the intake opening 266 is fed through an air passageway 268 to the blower chamber 252.

Each of the aroma cartridges other than the aroma cartridge 132 also includes a micro blower 234 to feed air into the aroma cartridge through the opening on the back side. By operating the micro blowers 234 independently, a predetermined aroma cartridge is able to be controlled to emit the scented air at a predetermined timing for a predetermined time period. A micro blower 184 of the mechanism to emit scent-free air shown in FIG. 3 also includes the same or similar structure as this micro blower. Accordingly, the micro blower 185 is able to emit air at a predetermined timing for a predetermined time period from opening 68 shown in FIGS. 1 to 3. The micro blower 184 is larger than the other micro blowers 234. Accordingly, the amount of air emitted from the opening 68 is far larger than the micro blowers 234, and the micro blower 184 is able to easily dissipate any scent lingering near the opening section 64 or carry a scent farther.

However, the micro blower 184 feeds air by the vibration of a piezoelectric element, as shown in FIG. 4. While the micro blower 184 has a fast response with a low level noise, the amount of air that is able to be fed from the micro blower 184 is structurally limited. Therefore, in order to spread a scent from the aroma cartridge to a wide space or to carry a scent afar, the air from the micro blower 184 on its own is insufficient. Though the micro blower 184 may be replaced with a larger fan, including a larger fan may generate increased acoustic noise when generating air flow of a certain volume, in contrast to a quiet operation comparable to the micro blower 184.

Therefore, a first preferred embodiment of the present invention includes a booster that includes a fan and surrounds the aroma display 50 to spread a scent from the aroma display 50 far and wide or to quickly dissipate the scent.

Figure 5:
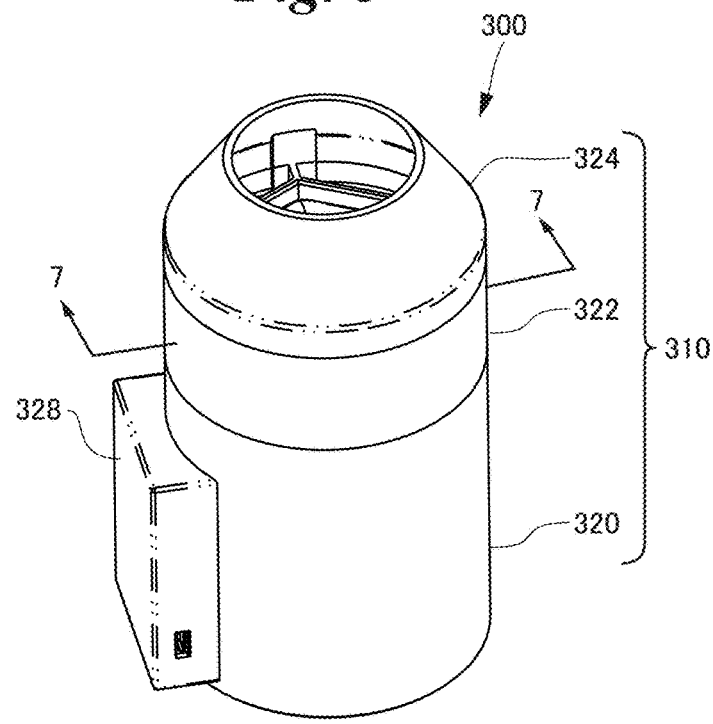
FIG. 5 is a perspective view of a booster device of an aroma display in accordance with a first preferred embodiment of the present invention.
Figure 8:
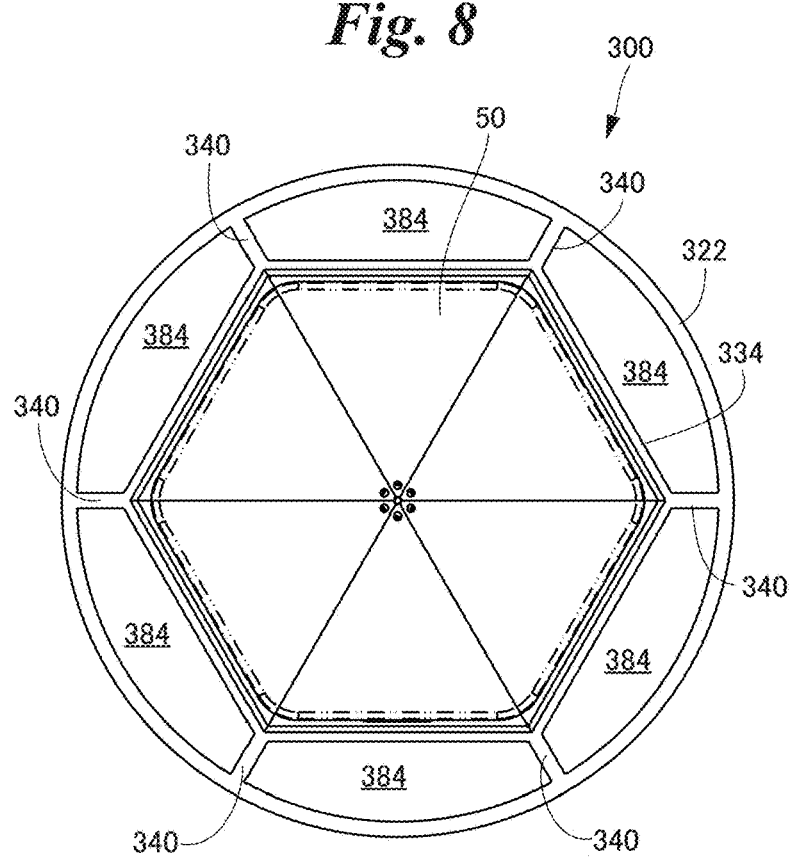
FIG. 8 is a cross-sectional view taken along the line 8-8 of an upper case of the booster device shown in FIG. 7.
Figure 6:
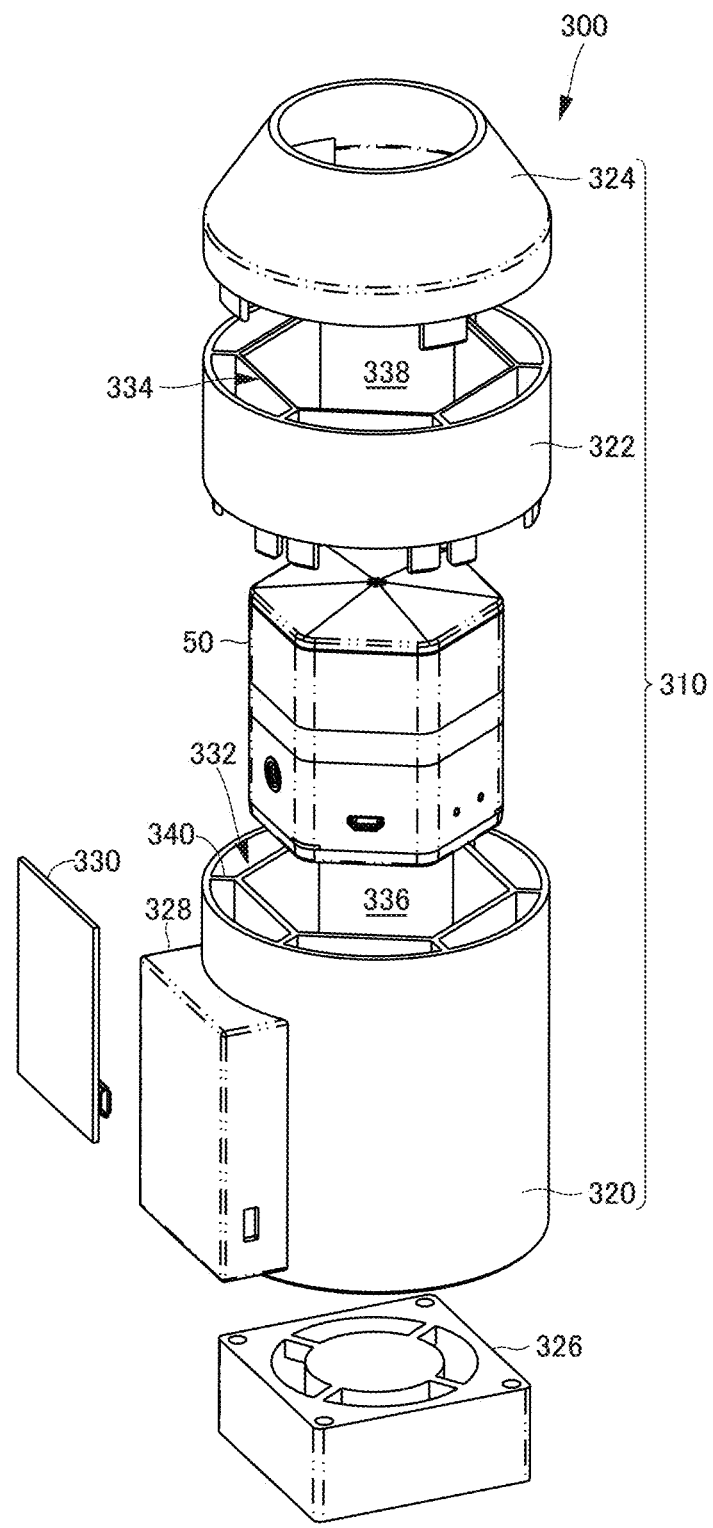
FIG. 6 is an exploded perspective view of the booster device shown in FIG. 5.
Figure 7:
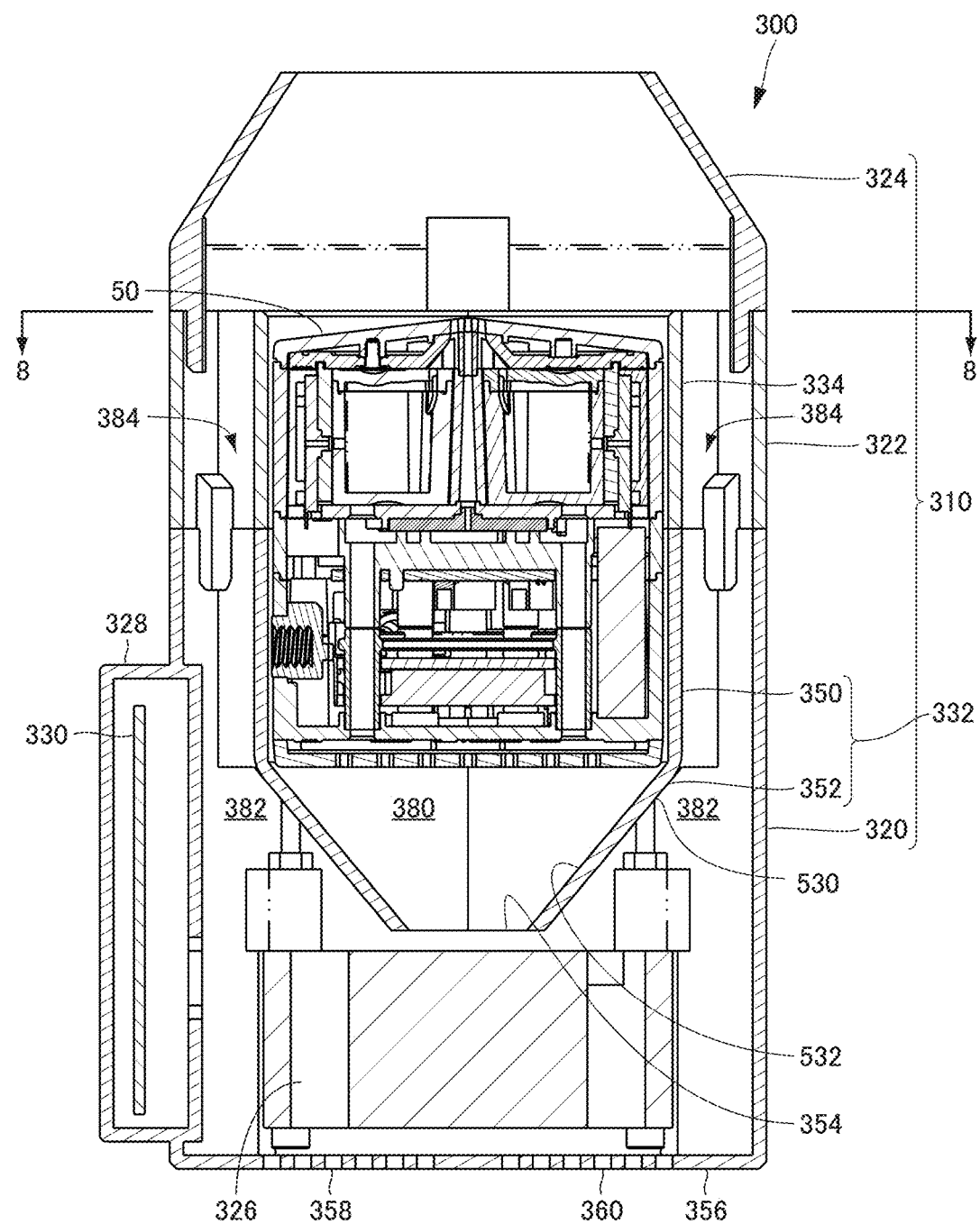
FIG. 7 is a cross-sectional view taken along the line 7-7 of the booster device shown in FIG. 5.

FIG. 5 shows an appearance of a booster 300 in accordance with the first preferred embodiment of the present invention, and FIG. 6 is an exploded perspective view thereof. FIG. 7 is a cross-sectional view taken along the line 7-7 of the booster 300 shown in FIG. 5. FIG. 8 is a cross-sectional view taken along the line 8-8 of an upper case of the booster 300 shown in FIG. 7.

Referring to FIGS. 5 to 8, the booster 300 includes a columnar housing 310 of a circular or substantially circular cross-section with a central axis, in which the aroma display 50 is included. The housing 310 includes a lower case 320 provided with a fan 326 therein and including a container portion 336 in which a lower portion of the aroma display 50 is provided, an upper case 322 attached to an upper portion of the lower case 320 and including a container portion 338 in which an upper portion of the aroma display 50 is provided, and a conical cap 324 including a circular or substantially circular cross-section attached to an upper portion of the upper case 322 where the circle diameter becomes smaller as a function of the distance from upper case 322. A cap 324 is open at upper and lower ends. The shape of the cap 324, as will be described later, squeezes the air flow generated by the fan 326 at the upper portion of the upper case 322 and thus to increase the velocity of air flow.

A partition 332 including a hexagonal or substantially hexagonal cross section defining a container portion 336 and holding side surfaces of the aroma display 50 is provided in the lower case 320. The partition 332 is fixed to an interior of the lower case 320 by a connector 340 that couples the lower half of each corner of the hexagon with the inner surface of the lower case 320. As shown in FIG. 8, each of the aroma display 50 and the housing 310 has a central axis, and the partition 332 holds the aroma display 50 with the central axis of the aroma display 50 and the central axis of the housing 310 parallel or substantially parallel to and aligned with each other.

A board structure 328, in which a control board 330 is provided, is located at a portion on an outer periphery of the lower case 320. As shown in FIG. 7, the partition 332 includes a cylindrical portion 350 opened at upper and lower ends, with a size and shape that fits and holds the aroma display 50 therein, and a conical section 352 extending downward from the lower opening of the cylindrical portion 350, including a conical shape opened at upper and lower ends, to divide the air flow from the fan 326 to an interior and an exterior of the cylindrical portion 350. The conical section 352 includes outer and inner side surfaces 530 and 532 and an opening 354 at a lower end. A cross-section of the partition 332 has a shape and size such that the aroma display 50 fits an interior of the partition 332. The conical section 352 is tapered with its inner diameter becoming smaller downward and, therefore, the aroma display 50 is supported by the conical section 352 at a boundary between the lower end of the cylindrical portion 350 and the upper end of the conical section 352 and fixed inside the housing 310. Here, the central axis of the aroma display 50 is aligned with the central axis of the housing 310.

The upper case 322 also includes a partition 334 defining the container portion 338. Referring to FIGS. 7 and 8, a cross-section of the partition 334 has a hexagonal shape that fits the housing of the aroma display 50. A height of the upper case 322 to make, as is shown in FIG. 7, the top position of aroma display 50 even or substantially even with the upper end of the partition 332 when the aroma display 50 is included in the housing 310. Upper ends of sides corresponding to respective vertexes of the hexagon of the partition 334 are connected to the inner surface of an upper case 322 by a structure 340. As can be particularly well seen from FIG. 8, between the outer surface of the partition 334 and the inner surface of the upper case 322, air passages 384 are provided, which will be described later.

A lower case 320 includes a bottom plate 356 with a plurality of air inlets 358-360 to intake air. On the bottom plate 356, a fan 326 is mounted. The fan 326 is adapted to take air in from the air inlets 358-360 provided in the bottom plate 356, and to generate air flow in the direction of the aroma display 50 in the housing 310. In the present preferred embodiment, the diameter of the fan 326 is larger than the inner diameter of the opening 354. A space is provided between the lower end of the conical section 352 and the upper end of the fan 326. In the present preferred embodiment, the fan 326 is driven by a DC-driven motor, and a maximum air flow rate of the fan is larger than a maximum air flow rate of the micro blower 184 that defines the air emission mechanism of the aroma display 50. The fan 326 spreads far and wide the scent emitted from the aroma display 50 or quickly dissipates any scent lingering rather widely around the booster 300. Therefore, the maximum air flow rate of the fan 326 is preferably far larger than the maximum air flow rate of the micro blower 184, for example. As an example, the maximum air flow of fan 326 is preferably about 5 times, more preferably about 10 times, and further preferably about 50 times or more of the maximum air flow rate of the micro blower 184. Accordingly, the air flow rate of the fan 326 is preferably adjustable, for example. If the size of the fan 326 is too large, the booster 300 becomes less portable and, therefore, the size of the fan 326 is limited by itself. The fan 326 is provided inside the booster 300. Accordingly, noise generated by operation of the fan 326 is able to be reduced.

Particularly referring to FIG. 7, in the booster 300 including the above-described structure, the interior of the housing 310 is divided, by partitions 332 and 334, to define an inner space 380 holding the aroma display 50 and air passages 382 and 384 that are outside of the space and defined as a ring-shaped space surrounding the aroma display 50, and joined at the portion of the cap 324. A plurality of openings are also provided at the bottom portion of the aroma display 50, and the micro blower 184 and the like of the aroma display 50 take air in from space 380 and uses it to emit scent from an aroma cartridge. An air passage 382 is defined by the outer side surface of the conical section 352 and the inner side surface of the lower case 320. An air passage 384 is a channel further downstream of the air passage 382 and, as shown in FIGS. 7 and 8, the air passage 384 is defined by the outer side surface of the partition 334 and the inner side surface of the upper case 322. Cross sections of the air passages 382 and 384 are reduced around the aroma display 50, accelerating air flow at this portion.

The cap 324 is detachable from the upper case 322. By removing the cap 324 from the upper case 322, the aroma display 50 can be removed from the booster 300. The aroma display 50 can be mounted on the booster 300 by the reverse procedure. If the upper case 322 is made detachable from lower case 320, attachment/detachment of the aroma display 50 becomes easier.

The control board 330 is connected by a cable, not shown, to a connector 66 and the fan 326 of the aroma display 50, feeding power to various electronic components in the aroma display 50 and the booster 300. Further, the control board 330 drives the fan 326 in accordance with an external control signal. In the present preferred embodiment, the aroma display 50 performs wireless communication, and the aroma display 50 is able to directly communicate with an external control device. The present invention, however, is not limited to the structure and operation described above. The control board 330 may transmit a control signal to the interior of the aroma display 50 through the connector 66, or the control board 330 may relay an output signal from the aroma display 50 to an external control device.

The aroma display 50 and the booster 300 described above operate as described below.

First, a user inserts necessary aroma cartridges into the aroma display 50. The user removes the cap 324 from the booster 300 and puts the aroma display 50 into housing 310. FIG. 7 shows a cross section at this time of the booster 300.

For example, a scenario may be provided for a movie reproduced on a PC, for example, to emit a specific scent identified by the identifier at a specific scene for a specific time period in synchronization with the movie. Then the PC reads the scenario and reproduces the scenario in synchronization with the movie. Specifically, the PC transmits a command to the wireless communication device of the aroma display 50 and a specific scent is emitted from the aroma cartridge with the designated identifier at the timing designated by the scenario. Receiving the command, the wireless communication device applies AC voltage at the designated timing for the designated time period to the micro blower 234 of the cartridge loading section loaded with the designated scent. Accordingly, the designated scent is emitted from the aroma display 50 at the timing and for the duration as designated by the scenario.

The micro blower 184 inside the aroma display 50 or the fan 326 in the housing 310 may be controlled to be operated simultaneously with the emission of a scent. When the micro blower 184 is in operation, scent-free air is emitted to an exterior of the aroma display 50 from the opening 68 shown in FIGS. 1 and 3. Together with this air flow, a scent from an aroma cartridge flows out from cap 324 of the booster 300. Accordingly, the user is able to observe the scent. In this case, however, the air flow generated by the micro blower 184 is weak and does not reach very far. Therefore, the scent is observed only in a close vicinity of the booster 300.

Figure 9:
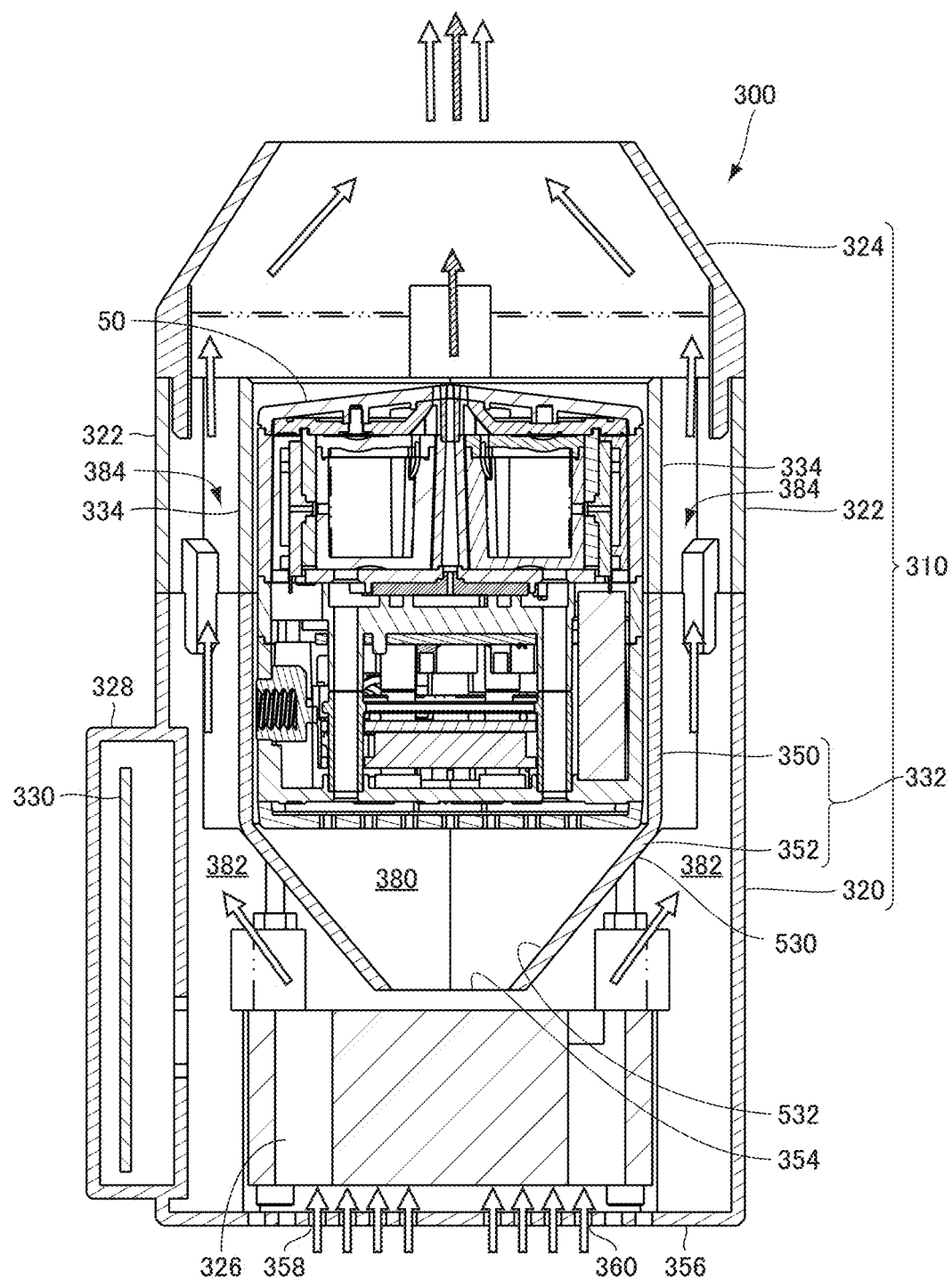
FIG. 9 is a cross-sectional view showing air flow in the booster device shown in FIG. 5.

FIG. 9 shows air flow in the booster 300 when the fan 326 is driven and the micro blower 184 is not driven. Referring to FIG. 9, the air flow generated by the fan 326 is represented by white arrows, and the flow of scented air emitted by the aroma display 50 is represented by hatched arrows. Referring to FIG. 9, the fan 326 takes in air and, through inlets 358-360 provided in the bottom plate 356, air is introduced to the interior of the housing 310. Since the interior of the conical section 352 is closed by the aroma display 50, the air flow generated by the fan 326 goes toward the ring-shaped air passage 382. This air flow is accelerated through the air passages 382 and 384 around the aroma display 50 and fed to the cap 324. The scent let out from the tip end of the aroma display 50 is emitted from the housing 310 with velocity far higher than that caused by the micro blower 184, because of the air flow that has passed through the air passages 382 and 384. Accordingly, the air flow reaches farther.

When the scent emitted from the housing 310 is to be dissipated, the operation of various components is the same as or similar to when the scent is emitted, except that no scent is emitted from the aroma display 50. By emitting scent-free air to an exterior of the booster 300 using the fan 326, not only the scent lingering near the booster 300 but also the scent lingering considerably far is able to be quickly dissipated and blown away. Thus, the scent can be dissipated powerfully, and the possibility of unintentionally mixing with the next emitted scent is reduced.

When the micro blower 184 is used, the air flow is weak and, therefore, only the scent lingering in the vicinity of the booster 300 is able to be dissipated.

As described above, by the present preferred embodiment, the scent generated by the aroma display 50 can be carried far and wide by using the fan 326. Further, the scent lingering in a wide range is able to be quickly dissipated. In addition, only the scent-free air is able to be emitted to a far distance. Accordingly, a scent is able to be emitted throughout a wide area and the mixing of scents is able to be prevented when the scents are switched.

When the aroma display 50 and the booster 300 are operated with a PC on one's desktop, it is unnecessary to operate the fan 326. Operation of the micro blower 184 is sufficient to personally enjoy a program with scents.

Further, according to this preferred embodiment, the aroma display 50 is able to be freely be attached to/detached from the booster 300. Therefore, for example, a plurality of the aroma displays 50 loaded with different aroma cartridges may be switched easily for use. Further, the aroma display 50 is able to be removed from the booster 300, and the aroma display 50 may be operated by itself.

The aroma display 50 in accordance with the first preferred embodiment described above provides emission of a scent to a wider space or dissipation of a scent from a wider space as compared with a conventional aroma display. Accordingly, operation of the aroma display 50 is able to be widened from personal use to more general use by a larger number of people. However, further improvements may be provided to let users more fully enjoy the scents.

In a real life setting, a scent is experienced not only by olfaction or sense of smell. In most cases, a scent is experienced with temperature. As an example, when one takes a sip of coffee, the aroma of coffee is experienced with its warmth. On the contrary, one experiences the scent of plants and trees with coolness in morning winds in the grass or in the forest.

A second preferred embodiment of the present invention has provides only the function of emitting scents but also a function of heating or cooling the air containing scent, fit for the scene when the scent is presented.

Figure 10:
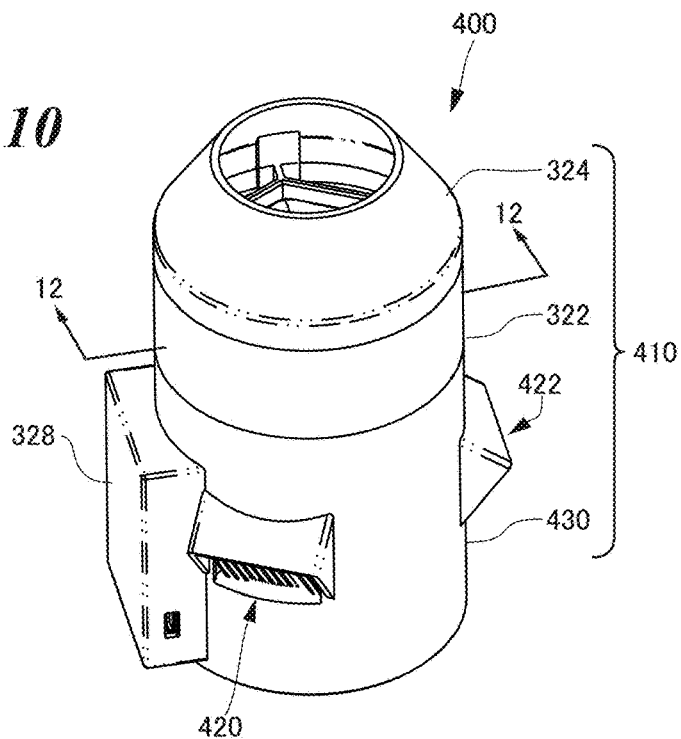
FIG. 10 is an oblique downwards perspective view of a booster device of an aroma display in accordance with a second preferred embodiment of the present invention.
Figure 11:
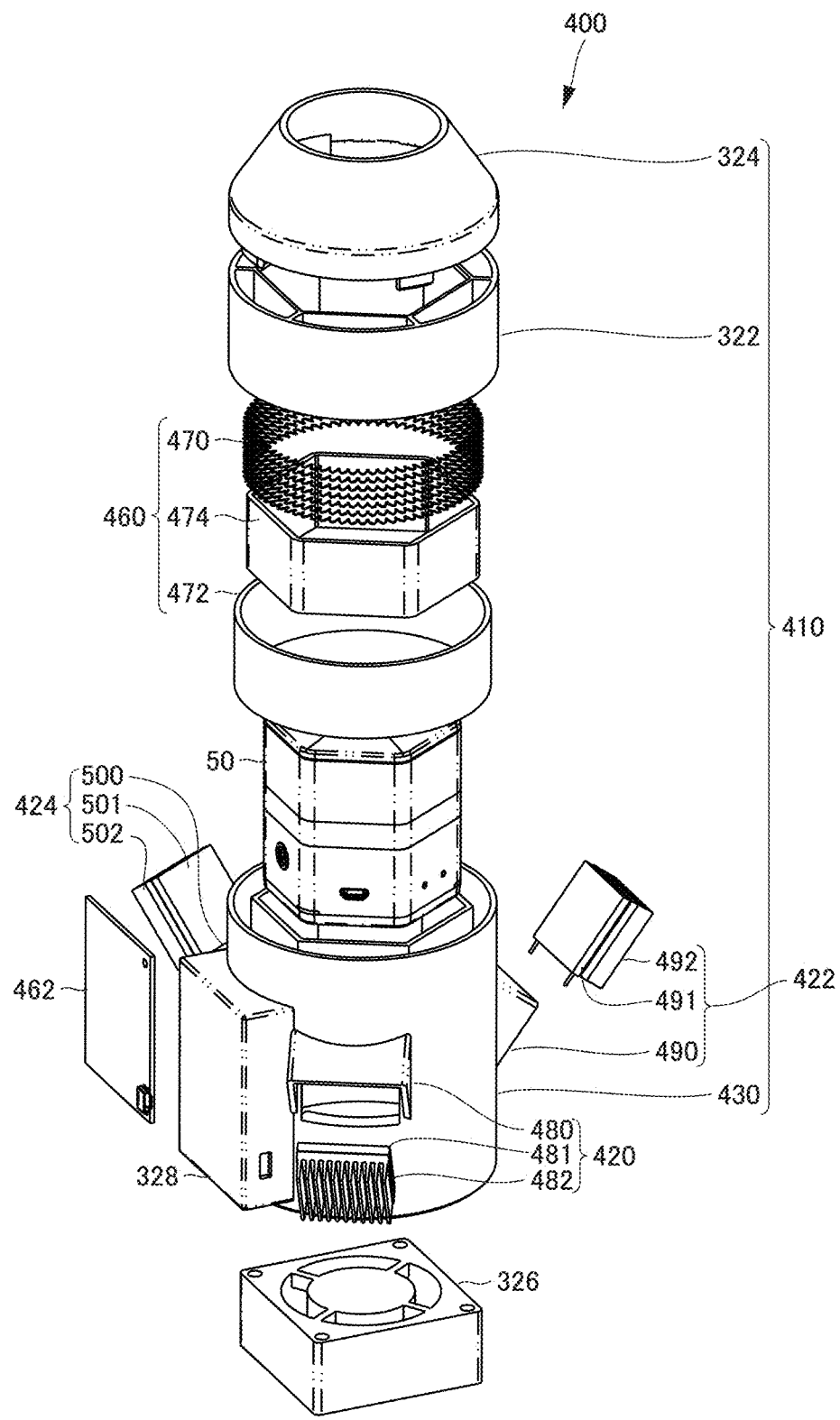
FIG. 11 is an exploded perspective view of the booster device shown in FIG. 10.
Figure 12:
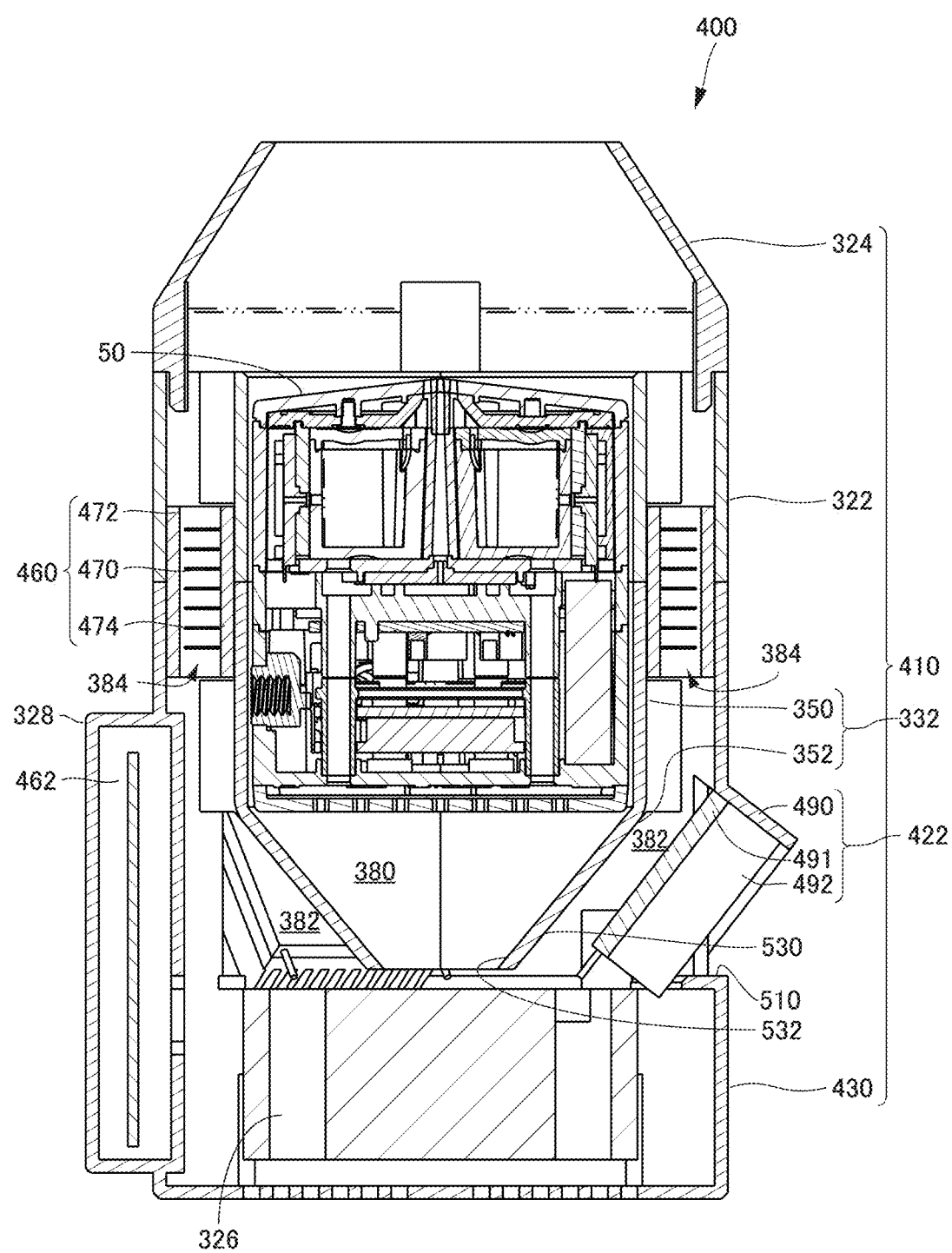
FIG. 12 is a cross-sectional view taken along the line 12-12 of the booster device shown in FIG. 10.

FIG. 10 shows an appearance of a booster 400 for an aroma display in accordance with the second preferred embodiment. FIG. 11 is an exploded perspective view of booster 400. FIG. 12 is a cross-sectional view taken along the line 12-12 of FIG. 10. Referring to FIGS. 10 to 12, booster 400 includes a housing 410, of which appearance is different from that of housing 310 in accordance with the first preferred embodiment. The housing 410 includes a lower case 430 provided with a fan 326 therein and including a container portion in which a lower portion of the aroma display 50 is placed, and including three heat exchangers 420, 422 and 424 (the heat exchanger 424 is not shown in FIG. 10) in addition to the board structure 328 on its periphery, an upper case 322 attached to the upper portion of the lower case 430, and a cap 324 attached to the upper portion of the upper case 322.

Three heat exchangers 420, 422 and 424 all have the same or substantially the same structure. Referring to FIG. 12, as an example, the heat exchanger 422 includes a plate-shaped Peltier module 491 with a Peltier element, provided at an opening 510 opened on a side surface of the lower case 320 with the heat absorbing (heat radiating) side surface facing the air passage 382 outside the conical section 352, a heat sink 492 attached to the heat radiating (heat absorbing) side surface of the Peltier module 491, and an overhanging portion 490 provided above the opening 510 protruding like a visor and covering the upper surface of the heat sink 492. Similarly, the heat exchanger 420 includes an overhanging portion 480, a Peltier module 481 and a heat sink 482. The heat exchanger 424 includes an overhanging structure 500, a Peltier module 501 and a heat sink 502.

The Peltier module 491 is a plate-shaped semiconductor device and when a DC in a predetermined direction is applied, a heat absorbing surface of the Peltier module 491 cools an object that is in touch with the surface and radiates heat to a heat radiating surface of the Peltier module 491. When the direction of current is reversed, the heat absorbing and radiating surfaces are switched. In other words, the Peltier module 491 has a heat exchanging function. The width of the Peltier module 491 is equal or substantially equal to the width of opening 510, and the upper edge of the Peltier module 491 is in air-tight contact with an upper edge of the opening 510. The Peltier module 491 is attached to the lower case 320 a lower edge of the Peltier module 491 is positioned farther in from the side surface of the lower case 320. Therefore, the air flow generated by the fan 326 is split by the Peltier module 491 to the two sides thereof.

A heater 460 to heat air that passes through the air passage 384 is provided in the upper case 322. The heater 460 includes a cylindrical outer heat insulator 472 provided to be in contact with an inner surface of the upper case 322, a cylindrical inner heat insulator 474 provided to be in contact with an outer side surface of the cylindrical portion 350, and a nichrome wire 470 wound a number of times around the inner heat insulator 474, provided between the outer and inner heat insulators 472 and 474. The nichrome wire 470 generates heat when a current is passed therethrough. The inner heat insulator 474 protects scent sources in the aroma display 50 from the heated or cooled air in the air passage 384. Scent generating characteristics of scent sources change when scent sources are heated or cooled. Therefore, the inner heat insulator 474 is provided. The inner heat insulator 474 may be provided at a position and range to protect from heating and cooling at least the portion of the aroma display at which scent sources are positioned.

In the board structure 328, in place of the control board 330 of the first preferred embodiment, a control board 462 is provided, which controls the Peltier module 491 and the nichrome wire 470 in addition to the function of control board 330.

Except for the above structure and operation, the booster 400 includes the same or similar structure as that of the booster 300 in accordance with the first preferred embodiment. When the direction of current is reversed, the heat radiating surface and the cooling surface of the Peltier module 491 are switched. Therefore, the booster 400 is able to heat the air by reversing the direction of current fed to the Peltier module, rather than heating the air by using the nichrome wire. In that case, the nichrome wire 470 is unnecessary. Further, both the Peltier module 491 and the nichrome wire 470 may be operated to preheat the air by the Peltier module 491 and additionally heat the air by the nichrome wire 470. Such operation is able to be implemented by controlling signals or currents applied externally to the booster 400.

The operation of the booster 400 is the same as or similar to the operation of the booster 300 in accordance with the first preferred embodiment. The booster 400 is different from the booster 300 in that the booster 400 is able to heat or cool the air generated by the fan 326 and passing through the air passages 382 and 384, in response to an external control signal.

Figure 14:
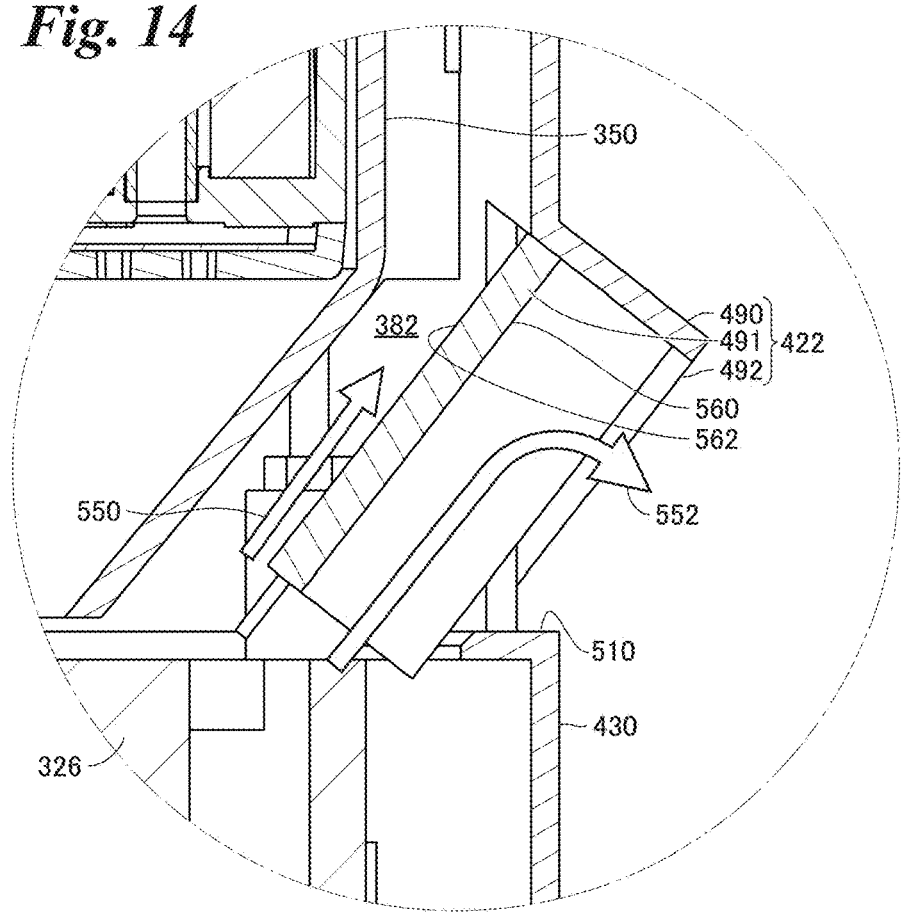
FIG. 14 is an enlarged cross-sectional view of a part of FIG. 13.
Figure 13:
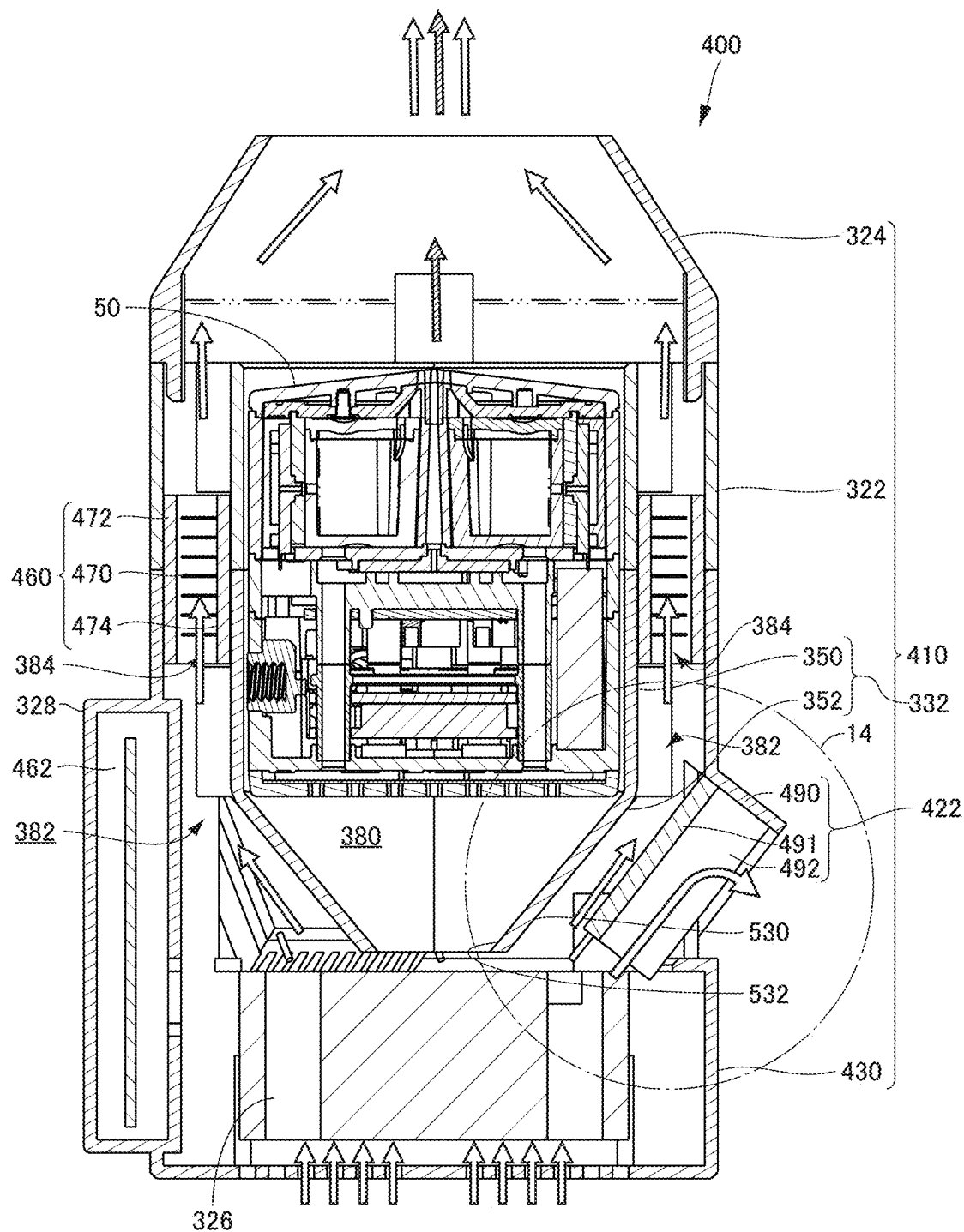
FIG. 13 is a cross-sectional view showing air flow in the booster device shown in FIG. 10.

FIG. 13 shows air flow when the booster 400 is in operation. In FIG. 13, white arrows indicate the flow of air generated by the fan 326, and hatched arrows indicate the flow of scented air emitted from the aroma display 50. FIG. 14 shows, in enlargement, the portion of FIG. 13 indicated by reference numeral 14. The flow of air in the booster 400 is the same as or similar to the flow of air in the booster 300 in accordance with the first preferred embodiment. What is different is that the air passing through the air passages 382 and 384 can be cooled or heated.

Particularly with reference to FIG. 14, a portion of the air generated by the fan 326 will be an air flow 550 that flows through the air passage 382 between the conical section 352 and the heat absorbing surface 562 of the Peltier module 491. The air flow 550 is deprived of its heat by the heat absorbing surface 562 and cooled. Another portion of air generated by the fan 326 is an air flow 552 split from the air flow 550 by the Peltier module 491 and guided to the side of the heat radiating surface 560 of the Peltier module 491, which air flow deprives the heat radiating surface 560 of heat and passes through the heat sink 492, to be discharged outside from an opening of the heat sink 492.

As an example, by feeding DC to the Peltier module 491 while driving the fan 326, the air flowing through the air passages 382 and 384 is able to be cooled, and thus a scent emitted from the aroma display 50 is able to be carried and spread with cold air. For example, while beautiful scenery of a mountain in a fresh morning is displayed on a PC screen, cold air with a fresh scent is spread, and a user will have a highly realistic sensation of a morning in the mountain. A portion of the air flow from the fan 326 is guided by the Peltier module 491 to the side of the heat sink 492, deprives the radiating surface 560 of heat by the heat sink 492, and dissipates the heat into the surrounding air. Accordingly, the Peltier module 491 is able to be efficiently operated.

Alternatively, the air flowing through the air passages 382 and 384 is able to be heated by feeding current to the nichrome wire 470 without feeding any current to the Peltier module 491. For example, when a scene of pouring coffee is to be displayed on a PC as described above, the air is heated by feeding current to the nichrome wire 470 and a scent of coffee emitted from the aroma display 50 is carried with heated air. Accordingly, the scent of coffee spreads with warm air and the user is able to observe the realistic sense of tasting a cup of coffee.

As described above, by the booster 400 in accordance with the present preferred embodiment, in addition to simply spreading a scent, dissipating a scent at a predetermined timing, or switching scents, the temperature of air carrying the scent is able to be adjusted in accordance with the scent. Accordingly, communication by scents is able to have a stronger effect. If heat only generated by the nichrome wire 470 is not sufficient, the current applied to the Peltier module 491 may be reversed to preheat the air passing through the channel 384 and thus to increase the heating of the air. If the Peltier module 491 provides sufficient heating and cooling capacity, the nichrome wire 470 may be omitted.

The present invention has been described with reference to the preferred embodiments. However, the present invention is not limited to the preferred embodiments above. For example, in the preferred embodiments described above, the cross-sectional shape of the aroma display 50 is hexagonal or substantially hexagonal and may be loaded with up to six aroma cartridges, for example. However, the shape of the aroma display 50 is not limited to a hexagon. The cross-sectional shape of the aroma display 50 may be determined independent of the number of the aroma cartridges to be included therein, and the cross-sectional shape of the aroma display 50 may include a shape of which number of corners match the number of cartridges to be included.

Further, in the preferred embodiments above, the aroma display 50 is detachable from the booster 300 or 400. By including a detachable structure, the aroma display 50 may be removed from the booster 300 or 400 and used by itself. When the aroma display 50 is operated by itself, it is able to be operated personally on one's desktop, similar to a known aroma display. The present invention, however, is not limited to such preferred embodiments. Commercially, the aroma display 50 and the booster 300 or 400 may be sold separately or the aroma display 50 and the booster 300 or 400 may be sold as a set. When they are sold as a set, the aroma display 50 and the booster 300 or 400 may be packed separately, or packed with the aroma display 50 provided in the booster 300 or 400.

Further, in the second preferred embodiment, both the heater and the heat exchanger are included. The present invention, however, is not limited to the structure and operation described above. Only the heater or only the heat exchanger may be provided in the booster. The numbers and positions of the heaters and the heat exchangers are not limited to those on the booster 400 of the second preferred embodiment. Positions of the heaters and the heat exchangers may be switched.

By the aroma display booster 400 in accordance with the second preferred embodiment of the present invention a scent is able to be spread to or dissipated from a wider area as compared with the conventional aroma display, and a highly realistic sensation of life scenes is able to be provided with scent, thus providing more effective communication with scents. The structure for implementing the above features, however, is not limited to the structure described in the second preferred embodiment. A third preferred embodiment of the present invention described in the following provides features and advantages similar to the booster 400 of the second preferred embodiment with a different structure.

Figure 15:
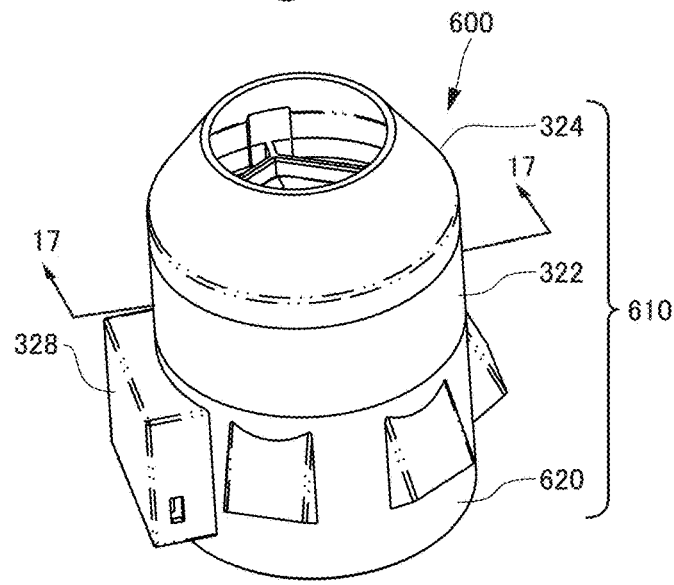
FIG. 15 is an oblique downwards perspective view of a booster device of an aroma display in accordance with a third preferred embodiment of the present invention.
Figure 17:
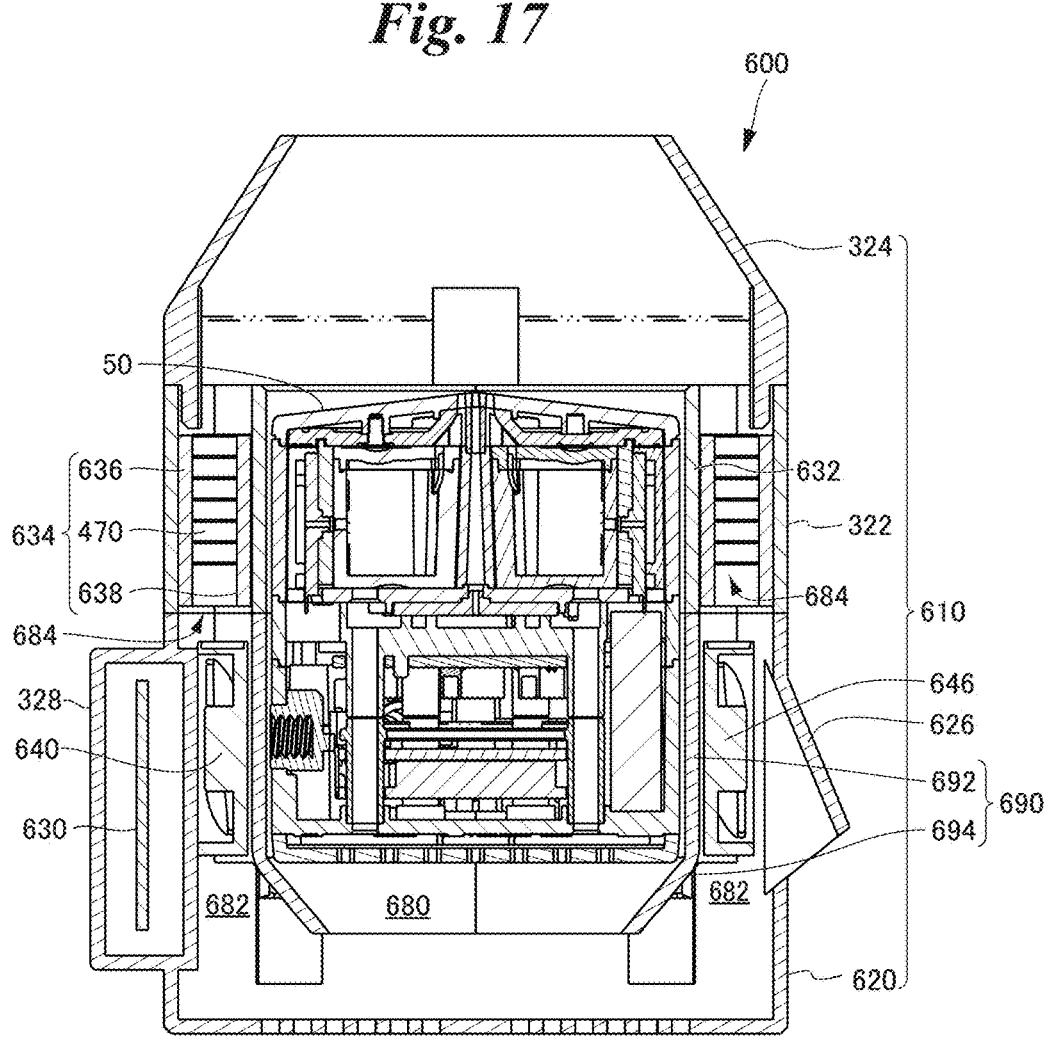
FIG. 17 is a cross-sectional view taken along the line 17-17 of the booster device shown in FIG. 15.
Figure 16:
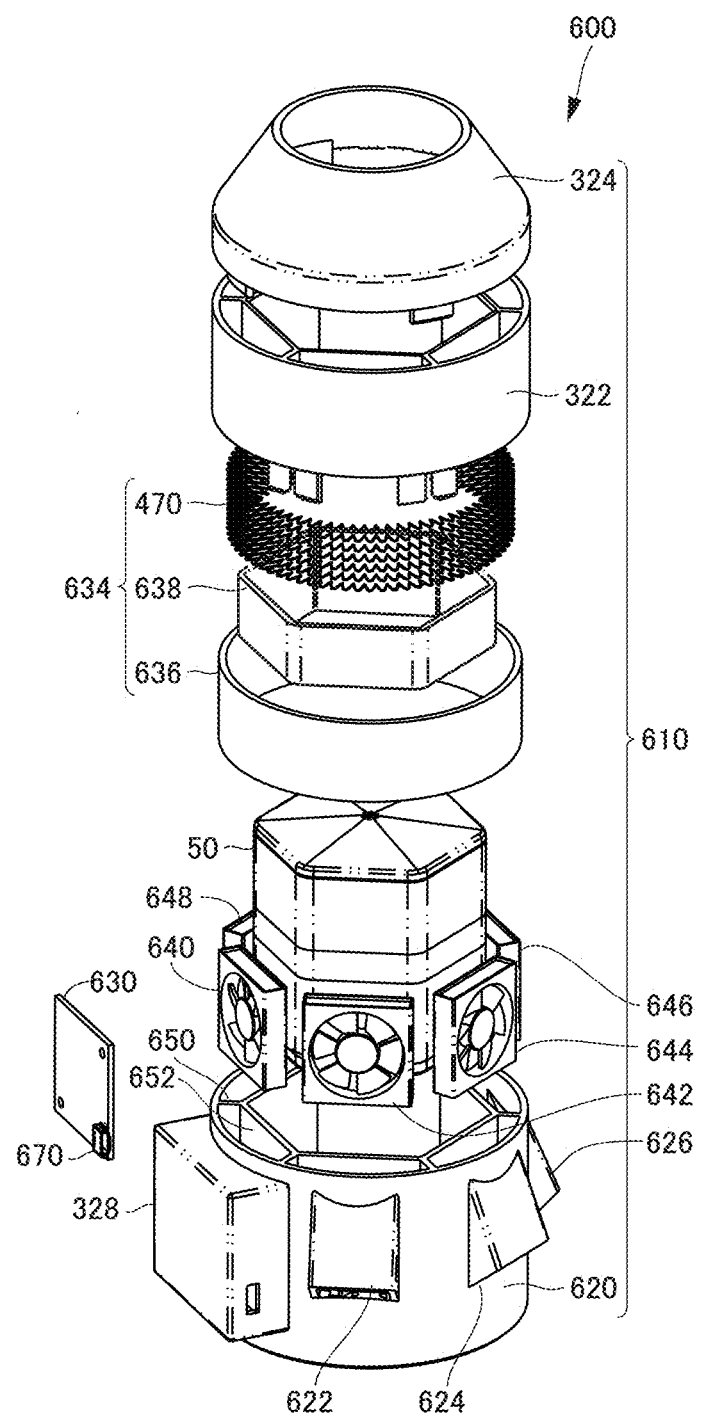
FIG. 16 is an exploded perspective view of the booster device shown in FIG. 15.

FIG. 15 shows an appearance of a booster 600 for an aroma display in accordance with the third preferred embodiment of the present invention. FIG. 16 is an exploded perspective view of the booster 600. FIG. 17 is a cross sectional view taken along the line 17-17 of FIG. 15. Referring to FIGS. 15 to 17, the booster 600 includes a housing 610 of which appearance is different from the housing 310 of booster 300 in accordance with the first preferred embodiment. The housing 610 includes a lower case 620 provided with small fans 640, 642, 644, 646, . . . 648 (as shown in FIG. 16) therein in place of the large fan 326 used in the second preferred embodiment, in which a lower portion of the aroma display 50 is positioned, an upper case 322 attached to the upper portion of the lower case 620, and a cap 324 attached to the upper portion of the upper case 322.

In the present preferred embodiment, six small fans, for example, the small fan 640, are located in six spaces defined by partitions 652 and 650 along an inner periphery of the lower case 620. At those portions of the lower case 620 which correspond to the small fans 640-648, the air inlets 622, 624, 626, etc. opened downward to feed air are defined, except for a portion corresponding to the small fan 640.

Referring to FIG. 16, in the present preferred embodiment, the small fans 640-648 are provided corresponding to respective aroma cartridges. The number of small fans 640 and the like, however, may be any number and not necessarily be the same as the number of aroma cartridges. Though the small fan 640 and other fans are preferably positioned at equal or substantially equal intervals along the inner periphery of the lower case 620, for example, the small fan 640 and other fans may be provided at other locations in accordance with preferred embodiments of the present invention.

Referring to FIG. 17, in the upper case 322, a partition 632 similar to the partition 334 (see FIG. 7) of the second preferred embodiment is provided, dividing the interior of the upper case 322 to a portion to receive the aroma display 50 and an air passage 684.

The lower case 620 is also divided by a partition 690 similar to the partition 652 of the second preferred embodiment to a portion receiving the aroma display 50 and a space 680 below, and an air passage 682. Similar to partition 332 shown in FIG. 7, the partition 690 includes a cylindrical portion 692 and a conical section 694 that divides the space below the aroma display 50 to an air passage 682 and a space 680 below the aroma display 50. The partition 632 and the cylindrical portion 692 have the same or substantially the same diameter and the air passages 682 and 684 define one continuous air passage. An upper portion of the air passage 682 is connected to an inner space of the cap 324.

As in the second preferred embodiment, in the upper case 322, a heater 634 is provided to heat air that passes through the air passage 684. The heater 634 includes a cylindrical outer heat insulator 636 provided to be in contact with an inner surface of the upper case 322, a cylindrical inner heat insulator 638 provided to be in contact with an outer side surface of the partition 632, and a nichrome wire 470 wound a number of times around the inner heat insulator 638, provided between the outer and inner heat insulators 636 and 638.

In the board structure 328, in place of the control board 462 of the second preferred embodiment, a control board 630 is provided, which controls the small fans 640-648 and the nichrome wire 470 in addition to the operation of the control board 330 of the first preferred embodiment. A USB connector 670 for an external connection is provided on the control board 630.

Except for the above structure and operation, the booster 600 has the same or similar structure as that of the booster 300 in accordance with the first preferred embodiment.

The operation of the booster 600 is the same as or similar to the operation of the booster 300 in accordance with the first preferred embodiment. The booster 600 is different from the booster 300 in that in response to an external control signal, small fans 640, 642, 644, etc. and the like take in air from an exterior of the booster 600 through the air inlets 622, 624, 626, etc. to generate air flow, which is fed to the air passage 684.

The air flow when the booster 600 is in operation is similar to the air flow shown in FIG. 9, and the only difference is that the small fans 640, 642, 644 and the like take in open air through the air inlets 622, 624, 626, etc. to generate air flow. Further, the present preferred embodiment differs, as does the second preferred embodiment, from the example shown in FIG. 9 in that the air passing through the air passage 684 is able to be heated.

As described above, by the booster 600 in accordance with the present preferred embodiment, in addition to simply spreading a scent, dissipating a scent at a predetermined timing, or switching scents, the air carrying the scent is able to be heated in accordance with the scent. Accordingly, communication with scents is able to be provided with an increased effect.

The preferred embodiments as have been described here are mere examples and should not be interpreted as restrictive. The scope of the present invention is determined by each of the claims with appropriate consideration of the written description of the preferred embodiments and embraces modifications within the meaning of, and equivalence to, the languages in the claims.

The booster for an aroma display is applicable to a wide range of industries including advertisement using scents, promotion for aroma-related products, for example, perfumes, presentations using scents at movie theaters, with movie-reproducing apparatuses, with broadcast receivers, for example, televisions, at planetarium halls and schools, within the medical field, for example, for treatment of anosmia, for presentation of educational materials for aroma therapists or perfumers, within the educational field for children or people with weak cognition of scents, and as a tool for better sleep environments to provide smooth sleep onset and refreshing awakening.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A booster device for an aroma display, the aroma display including a columnar shape with first and second surfaces and a side surface, the first surface including an emitting opening to emit a scent, and a wind source to emit the scent to an exterior of the aroma display is provided in the aroma display, a maximum air flow generated by the wind source being substantially equal to or smaller than a predetermined value, the booster device comprising:
   a housing detachably accommodating the aroma display; and
   a fan provided in the housing to generate a maximum air flow that is larger than the predetermined value; wherein
   the housing includes a cylindrical outer housing including a bottom surface with an air inlet to take in air and a cap with an opening, and a holder to hold the aroma display in the housing with the emitting opening of the aroma display facing the opening;
   the holder holds the aroma display to define an air passage between the outer housing and the aroma display;
   the fan is provided in the housing to blow out air to the air passage; and
   the cap includes a conical or substantially conical structure to narrow the air flow generated by the fan, provided at an end portion of the outer housing on a side of the first surface of the aroma display.

2. The booster device for an aroma display according to claim 1, wherein each of the aroma display and the outer housing has a central axis, and the holder holds the aroma display with the central axes of the aroma display and the outer housing parallel or substantially to each other.

3. The booster device for an aroma display according to claim 2, wherein the holder holds the aroma display with the central axis of the aroma display aligned with the central axis of the outer housing.

4. The booster device for an aroma display according to claim 1, further comprising a heater provided in the air passage to heat air passing through the air passage.

5. The booster device for an aroma display according to claim 1, further comprising a heat exchanger provided in the outer housing to conduct heat exchange between the air passing through the air passage and air outside the outer housing.

6. The booster device for an aroma display according to claim 5, wherein the heat exchanger is provided to discharge heat of the air passing through the air passage to the exterior of the outer housing and to cool the air passing through the air passage.

7. The booster device for an aroma display according to claim 5, wherein the heat exchanger is provided to introduce heat of the air outside the outer housing into the outer housing to heat the air passing through the air passage.

8. The booster device for an aroma display according to claim 5, wherein:
   an opening is provided on a side surface of the outer housing;
   the heat exchanger includes a Peltier module including first and second surfaces to contact respective objects of heat exchange; and
   the Peltier module is attached to the opening with the first surface facing the air passage and the second surface facing the exterior of the outer housing.

9. The booster device for an aroma display according to claim 8, further comprising:
- a heat sink provided on the second surface of the Peltier module; wherein
- the Peltier module includes an upper edge with a same or substantially a same length as an edge at the upper end of the opening, and the upper edge is in contact with the edge at the upper end of the opening; and
- a lower end side of the Peltier module is located at a position to split air flow generated by the fan to the air passage side and to the heat sink side by the Peltier module.

10. The booster device for an aroma display according to claim 1, further comprising a heat insulator located between the air passage and the aroma display.

11. The booster device for an aroma display according to claim 10, wherein the heat insulator is located between the air passage and at least a portion of the aroma display which holds a scent component.

12. The booster device for an aroma display according to claim 1, further comprising a plurality of the fans located at equal or substantially equal intervals along an inner circumference of the housing at a portion surrounding the aroma display.

13. The booster device for an aroma display according to claim 1, wherein the fan is provided in the housing between the second surface of the aroma display including in the housing and the bottom surface of the housing.

\* \* \* \* \*